(12) United States Patent
Lehrburger et al.

(10) Patent No.: US 11,542,532 B2
(45) Date of Patent: Jan. 3, 2023

(54) APPARATUS AND PROCESS FOR TREATING BIOMASS FOR ON-SITE PRODUCTION OF CELLULOLYTIC ENZYMES AND METHOD OF USING THE ENZYMES TO MANUFACTURE FUELS AND CHEMICALS

(71) Applicants: Auburn University, Auburn, AL (US); PureVision Technology LLC, Fort Lupton, CO (US)

(72) Inventors: Edwin R. Lehrburger, Fort Lupton, CO (US); Dhrubojyoti D. Laskar, Fort Lupton, CO (US); Zhihua Jiang, Auburn, AL (US); Jing Li, Auburn, AL (US); Harry Cullinan, Opelika, AL (US); Yoon Y. Lee, Auburn, AL (US)

(73) Assignees: Auburn University, Auburn, AL (US); PureVision Technology LLC, Fort Lupton, CO (US)

( * ) Notice: Subject to any disclaimer, the term of this patent is extended or adjusted under 35 U.S.C. 154(b) by 0 days.

(21) Appl. No.: 17/697,703

(22) Filed: Mar. 17, 2022

(65) Prior Publication Data
US 2022/0298531 A1    Sep. 22, 2022

Related U.S. Application Data

(60) Provisional application No. 63/162,623, filed on Mar. 18, 2021.

(51) Int. Cl.
*C12P 7/10* (2006.01)
*C13K 1/02* (2006.01)
(Continued)

(52) U.S. Cl.
CPC .......... *C12P 7/10* (2013.01); *C08B 37/0057* (2013.01); *C08H 8/00* (2013.01); *C12P 19/02* (2013.01);
(Continued)

(58) Field of Classification Search
CPC ........................... C12Y 302/0121; C12P 7/10
See application file for complete search history.

(56) References Cited

U.S. PATENT DOCUMENTS

| 4,461,648 A * | 7/1984 | Foody ...................... D21B 1/12 435/165 |
| 2017/0247730 A1 | 8/2017 | Brown et al. |

FOREIGN PATENT DOCUMENTS

| WO | 2019010576 A1 | 1/2019 |

OTHER PUBLICATIONS

International Search Report and Written Opinion dated May 9, 2022, from the Australian Patent Office in connection with the International Application No. PCT/US2022/020800.

* cited by examiner

*Primary Examiner* — Tekchand Saidha
(74) *Attorney, Agent, or Firm* — Christopher M. Scherer; Joseph T. Leone; DeWitt LLP

(57) ABSTRACT

An integrated process and corresponding apparatus that produces a relatively clean, delignified cellulose product from lignocellulosic biomass. The method includes treating a portion of the delignified cellulose itself as a substrate to produce on-site cellulolytic enzymes, including further treating the remaining delignified cellulose with the resulting cellulolytic enzymes for in situ enzymatic hydrolysis. The process and apparatus are useful to produce fermentable sugars for cost-effective manufacturing of fermentable sugars, fuels, bioproducts and chemicals.

6 Claims, 10 Drawing Sheets

(51) Int. Cl.
  *C12P 19/02* (2006.01)
  *C12P 19/14* (2006.01)
  *C08B 37/00* (2006.01)
  *C13K 13/00* (2006.01)
  *C08H 8/00* (2010.01)
(52) U.S. Cl.
  CPC ................ *C12P 19/14* (2013.01); *C13K 1/02* (2013.01); *C13K 13/002* (2013.01); *C12P 2201/00* (2013.01)

APPARATUS AND PROCESS FOR TREATING BIOMASS FOR ON-SITE PRODUCTION OF CELLULOLYTIC ENZYMES AND METHOD OF USING THE ENZYMES TO MANUFACTURE FUELS AND CHEMICALS

CROSS-REFERENCE TO RELATED APPLICATIONS

Priority is hereby claimed to provisional application Ser. No. 63/162,623, filed Mar. 18, 2021, which is incorporated herein by reference.

FIELD OF THE INVENTION

Disclosed herein is a process of preparing cellulose fibers from lignocellulosic biomass. In the process, cellulose is separated rapidly from other constituents of lignocellulosic biomass and then used for 1) on-site production of cellulases and other cellulolytic enzymes; and 2) used as the primary substrate to manufacture fermentable sugars, fuels, and chemicals. The process incorporates in-situ enzymatic hydrolysis of pretreated biomass to yield fermentable sugars at greatly reduced cost. The overall process provides a low-cost, environmentally friendly route to convert lignocellulosic biomass to fermentable sugars, which can then be used to make biofuels, bioproducts, and chemicals.

BACKGROUND

Lignocellulosic plant biomass, being the primary source of renewable materials on earth, is a promising, renewable feedstock to make biofuels, bio-based chemicals, and other value-added products. Spurred by the need to address climate change, energy security, and depleted petroleum reserves, attention is currently directed toward developing novel, economically viable approaches to convert biomass into fuels and other bio-based products. This attention is due, in major part, to the ready availability of large amounts of renewable lignocellulosic biomass. Currently, a large portion of lignocellulosic biomass is burned for its thermal energy or landfilled. But its chemical potential—its usefulness as an alternative raw material to make products now made from petroleum—is a long-felt and unsatisfied need.

Lignocellulosic biomass is made up of three chemically distinct components: cellulose, hemicellulose and lignin. Cellulose, the primary component of biomass (representing up to 50% dry-weight) comprises long, linear fibrils of $\beta$-(1,4) glucopyranosides chains having a native degree of polymerization (DP) of roughly about 5000 to about 15000. In contrast, the hemicellulose fraction of biomass exhibits a much broader distribution of sugars. These include branched polysaccharides composed of 1,4-linked $\beta$-D-hexosyl residues having a typical DP from about 70 to about 200. The lignin component of biomass is the most intractable component of the plant. Lignin is essentially the structural scaffold of plant material; which enhances the rigidity of the cellulosic and hemicellulosic fiber network. Microorganisms and enzymes cannot effectively attack cellulose fibers present in biomass without prior treatment of the biomass to remove at least a fraction of the lignin. In its native form, the majority of cellulose in plant material is inaccessible to cellulolytic enzymes or bacteria due to the enveloping lignin scaffold. Lignin can also physically and/or chemically inhibit enzymatic degradation of cellulose in native biomass via irreversible enzyme absorption, thereby greatly limiting enzymatic hydrolysis efficacy. Therefore, removal of certain concentrations of lignin from cellulosic biomass will not only enhance enzyme accessibility but will reduce the amount of enzymes needed for hydrolysis and reduce enzyme nonspecific absorption on lignin, thereby significantly improving cellulolytic enzyme activity. Thus, for successful commercial use of biomass as an alternative feedstock for production of fuels and chemicals, separation of a relatively clean cellulose fraction with efficient lignin removal is imperative in concert with the production of on-site enzymes using the pretreated and hydrolyzed cellulose-rich biomass as the carbon source to grow the on-site enzymes.

Accordingly, converting lignocellulosic biomass into fuels, bioproducts and chemicals along the standard biochemical route entails a physicochemical pre-treatment of the biomass, followed by enzymatic hydrolysis of the polysaccharide components cellulose and hemicellulose into monomeric sugars. Conventional lignocellulosic biomass conversion approaches use thermochemical pre-treatment of biomass as the entry point into biorefinery schemes to produce delignified cellulose or pretreated biomass. The pretreated fraction is then subjected to enzymatic hydrolysis to yield monomeric sugars. Hence, various conventional pre-treatment processes have as their primary goal achieving higher sugar yields. Thus, conventionally, the raw biomass has been treated either with dilute acids or bases, or subjected to steam explosion, ammonia fiber explosion, sulfite pretreatment, treatment with organic solvents, etc. However, the major disadvantages of such conventional biomass pre-treatment approaches include: 1) high cost of chemical input; 2) high cost of capital equipment; 3) high operating costs of batch operations; and 4) high energy consumption. These conventional pre-treatment processes do not fill the market need for economically viable techniques to prepare high purity cellulose from lignocellulosic biomass, as either a final product per se or as an intermediate.

Also, current enzyme manufacturers produce highly refined cellulolytic enzyme cocktails composed of three primary cellulolytic enzymes (EC 3.2.1.x): endoglucanase (EC 3.2.1.6), cellobiohydrolase (CBH-1 & CBH-2; EC 3.2.1.91) and $\beta$-glucosidase (EC 3.2.1.21). These enzyme manufacturing companies have made great progress during the past twenty years in this highly specialized arena. But the cost of these purified cellulase enzymes is still too expensive to convert cellulosic biomass into fermentable sugars and ultimately produce affordable sugars, biofuels, bioproducts, and chemicals. One of the most expensive aspects of manufacturing cellulase enzymes is due to the methods to convert the crude broth of cellulase enzymes into a highly refined cellulase enzyme product. Moreover, costs associated with transporting such cellulolytic enzymes can become a limiting factor where there is no large-scale domestic industrial cellulase production facility that is immediately near the sources of biomass being grown and harvested. Thus, significant cost savings can be achieved if the needed cellulase enzymes are not transported, but rather are produced on-site. On-site production of cellulase enzymes will also render unnecessary additional processing steps typically taken 1) to manufacture highly refined cellulase enzymes; and 2) prior to transport, such as enzyme clarification and stabilization. In many industrial uses, the whole fungal fermentation broth can be used in the enzymatic hydrolysis process. If a portion of lignocellulosic biomass itself could be used as the raw material for production of cellulolytic enzyme, production cost of such enzymes could be further reduced substantially.

Consequently, there is an ongoing need for an art that is industrially feasible, economical, and simple to produce, partially delignified cellulose product from biomass for cost-effective enzymatic hydrolysis conversion into fermentation sugars. There is also a need for significantly reducing the high costs associated with cellulase enzyme production and transport by producing such enzymes at the site of use, where the raw biomass is pretreated to reduce the lignin content within the cellulose-rich substrate. There additionally is a need for methods in a biorefinery set up for on-site production of cellulose enzymes via fermentation using a portion of delignified cellulose as feedstock, while integrating processes for utilizing the resulting crude fungal fermentation broth for in-situ enzymatic hydrolysis of remaining cellulose to produce inexpensive monomeric sugars for efficient production of biofuels, chemicals, etc. These and other needs are addressed by the present disclosure.

SUMMARY

Aspects of the disclosure describe and validate effective, efficient, and economic conversion technologies to realize the potential of using various lignocellulosic feedstocks, from, for example, trees, grasses, energy crops and agricultural residues for the production, for example, of biomass-derived sustainable sugars, fuels, bioproducts and chemicals. In broad terms, this disclosure describes: an integrated process in a biorefinery set up comprising separating a fraction of cellulose from lignocellulosic biomass; then utilizing at least a portion of the cellulose as a substrate for on-site production of cellulolytic enzymes; further treating the remaining cellulose product with the resulting cellulolytic enzymes for in-situ enzymatic hydrolysis to produce fermentable sugars, and optionally co-fermenting the resulting sugars to ethanol, lactic acid, or other fermentation products.

Disclosed herein is an apparatus and process to prepare and fractionate cellulose-containing products from lignocellulosic biomass using hydrolysis chemistry with PureVision's patented continuous countercurrent reactor technology. (PureVision Technology, Inc. 511 McKinley Avenue, Fort Lupton, Colo. 80621, USA.) See U.S. Pat. Nos. 6,419,788; 6,620,292; 7,600,707; 7,717,364; and 8,136,747. The preferred continuous countercurrent reactor technology rapidly converts biomass into a solid cellulose-rich product and an extract liquor containing lignin and hydrolyzed hemicellulose or oligomeric xylose. Under enhanced hydrolysis conditions, the continuous countercurrent reactor produces >85% purity cellulose product with approximately 50%-90% of the lignin and hemicellulose removed.

Particular versions of the method include an apparatus and process to treat a portion of the produced cellulosic fraction for on-site cellulase production by aerobic fermentation using microorganisms, such as *Trichoderma reesei*, or any other suitable microorganism, without limitation, now known or developed in the future. The resulting crude fungal fermentation broth may be used for in situ enzymatic hydrolysis of the remaining continuous countercurrent reactor-derived cellulose fractions to yield fermentable sugars. Typically, the resulting sugar product has an overall glucan digestibility ranging from about 45% to about 80%.

Also disclosed herein is an integrated system to convert cellulosic biomass directly into sugars, fuels, and chemicals, incorporating processes to produce compositions of matter enriched in cellulose, to on-site cellulase production, to in situ enzymatic hydrolysis, and to co-fermentation to fuels and chemicals.

Thus, disclosed herein is a method of making a first composition of matter comprising cellulose, and a second composition of matter comprising hemicellulose-derived xylose and lignin, the method comprising:

in a continuous, counter-current extruder/reactor, admixing biomass and water for a time, and a temperature, and at an energy input, wherein a first, solid-phase composition of matter enriched in cellulose fibers is extruded from a first outlet of the extruder/reactor, and a second, liquid-phase composition of matter enriched in lignin and hemicellulose-derived xylose is extruded from a second outlet of the extruder reactor.

The first, solid-phase composition of matter comprises at least 80% cellulose. At least 50% of cellulose present in the biomass is present in the first, solid-phase composition of matter. The water-based reagent may further comprise an acid or a base dissolved therein. The biomass and the water-based reagent are mixed at a temperature of from about 150° C. to about 300° C.

The method further comprises enzymatically hydrolyzing at least a portion of the cellulose present in the first composition of matter to yield a third composition of matter comprising monomeric sugars.

The method further comprises fermenting at least a portion of the first composition of matter with a microorganism capable of fabricating cellulolytic enzymes using cellulose or hemicellulose as a source of carbon, for a time, at a temperature, and under suitable conditions to yield a composition of matter comprising at least one cellulolytic enzyme. At least a portion of the first composition of matter is fermented with a prokaryote or a eukaryote, aerobically or anaerobically.

The method further comprises enzymatically hydrolyzing at least a portion of the cellulose or hemicellulose present in the first composition of matter using the composition of matter comprising at least one cellulolytic enzyme to yield a third composition of matter comprising monomeric sugars.

The method further comprises fermenting at least a portion of the monomeric sugars present in the third composition of matter.

Also disclosed herein is a method of making and using enzymes in situ, the method comprising:
(a) in a continuous, counter-current extruder/reactor, admixing biomass and water for a time, and a temperature, and at an energy input, wherein a first, solid-phase composition of matter enriched in cellulose fibers is extruded from a first outlet of the extruder/reactor, and a second, liquid-phase composition of matter enriched in lignin and hemicellulose-derived xylose is extruded from a second outlet of the extruder reactor;
(b) fermenting in a vessel at least a portion of the first composition of matter with a microorganism capable of fabricating a desired cellulolytic enzyme using cellulose or hemicellulose as a source of carbon, for a time, at a temperature, and under suitable conditions to yield a third composition of matter comprising the desired cellulolytic enzyme;
(c) in the same vessel as step (b), using the third composition of matter to enzymatically hydrolyze remaining cellulose or hemicellulose to yield a fourth composition of matter comprising monomeric sugars.

The method further comprises:
(d) fermenting at least a portion of the monomeric sugars present in the fourth composition of matter.

In some versions, step (d) is conducted in the same vessel as steps (b) and (c).

Also disclosed herein is a method of making and using enzymes in situ, the method comprising:

(a) in a continuous, counter-current extruder/reactor, admixing biomass and water for a time, and a temperature, and at an energy input, wherein a first, solid-phase composition of matter enriched in cellulose fibers is extruded from a first outlet of the extruder/reactor, and a second, liquid-phase composition of matter enriched in lignin and hemicellulose-derived xylose is extruded from a second outlet of the extruder reactor;

(b) fermenting in a vessel at least a portion of the first composition of matter with a microorganism capable of fabricating a desired enzyme using cellulose or hemicellulose as a source of carbon, for a time, at a temperature, and under suitable conditions to yield a third composition of matter comprising the desired enzyme;

(c) using the third composition of matter to catalyze a reaction catalyzed by the desired enzyme.

Other objects, details and advantages will become apparent from the following drawings, detailed description, and examples.

DETAILED DESCRIPTION

Disclosed herein is an integrated biorefining process to separate a composition of matter comprised predominately of cellulose from lignocellulosic biomass such as found in trees, grasses, energy crops, and agricultural residues. This is followed by a novel fermentation step using a portion of the cellulose-containing composition as a substrate and carbon source for on-site production of cellulolytic enzymes. The remaining cellulose-containing product is then digested with the resulting cellulolytic enzymes to produce fermentable sugars.

Figure 1:
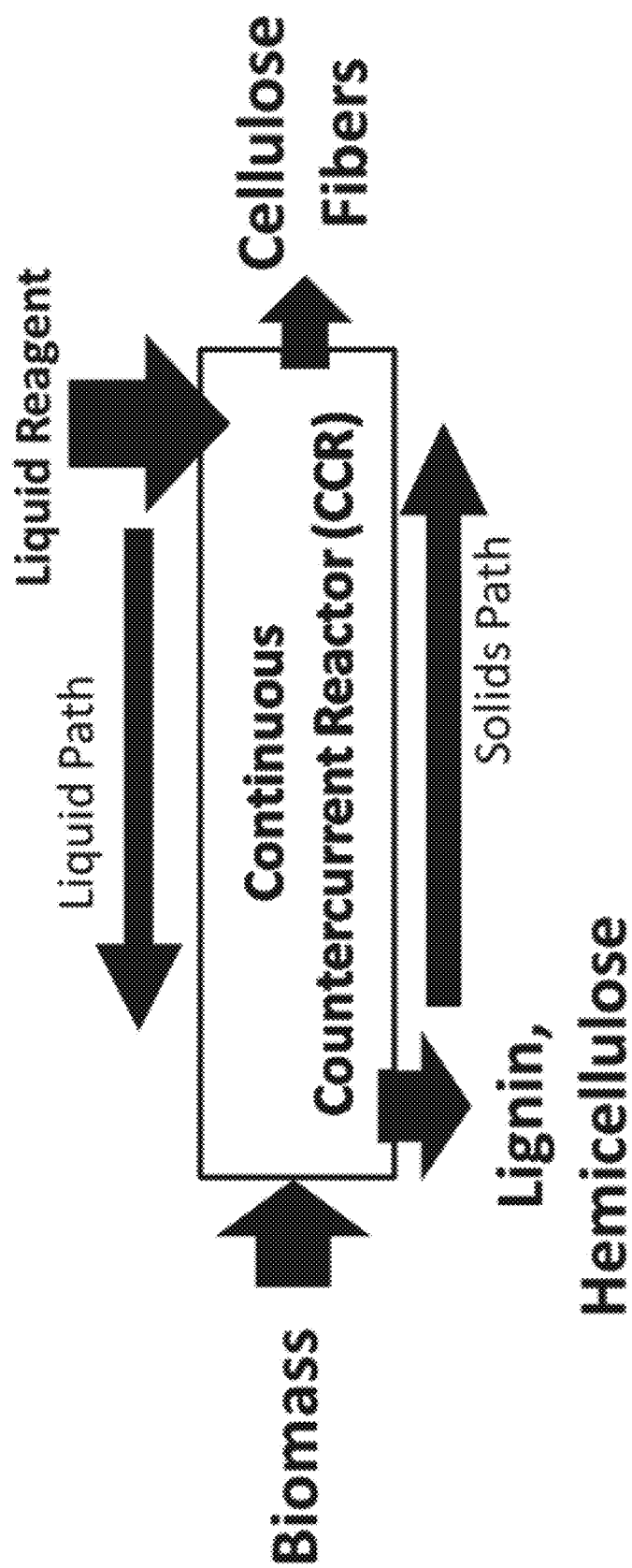
FIG. 1 is a conceptual diagram of a continuous countercurrent reactor wherein the liquids and solids pass each other in counterflow while being mixed and discharged continuously.

It has been found that cellulose-containing compositions with most of the lignin removed can be produced when lignocellulosic materials are treated with hot water and chemical reagents in a Continuous Countercurrent Reactor ("continuous countercurrent reactor") to remove hemicellulose hydrolysis products and to mobilize and remove lignin, extractives, and residual hemicellulose. A schematic diagram of a suitable continuous countercurrent reactor is shown in FIG. 1. The continuous countercurrent reactor was first developed by Dr. Richard Wingerson at PureVision Technology and is disclosed in several issued patents. (See U.S. Pat. Nos. 6,419,788; 6,620,292; 7,600,707; 7,717,364; and 8,136,747). The continuous countercurrent reactor was initially designed to be built using off-the-shelf components from a twin-screw extruder built to withstand over 3,000 psi and several hundred degrees Celsius, though the PureVision technology typically operates well below these limits. The continuous countercurrent reactor allows for a high temperature, continuous, countercurrent, liquid biomass extraction that yields one product stream containing cellulose-rich solids and a second liquid product stream containing other biomass components, namely solubilized lignin, xylose, and other extractives. In the continuous countercurrent reactor, the liquids and solids pass each other in counterflow while being mixed and discharged continuously. Reagents can be injected into the mix at any point along the length of the continuous countercurrent reactor. Added chemicals and water can be used to control staged fractionation and to control the liquor stream pH, which is often important for high product recovery. Temperature in the continuous countercurrent reactor can be controlled in many variations, including providing a lower-temperature zone near the liquid discharge end and a high-temperature zone near the solids discharge end. Multiple stages can be used to achieve higher purity of products or different products.

Figure 2:
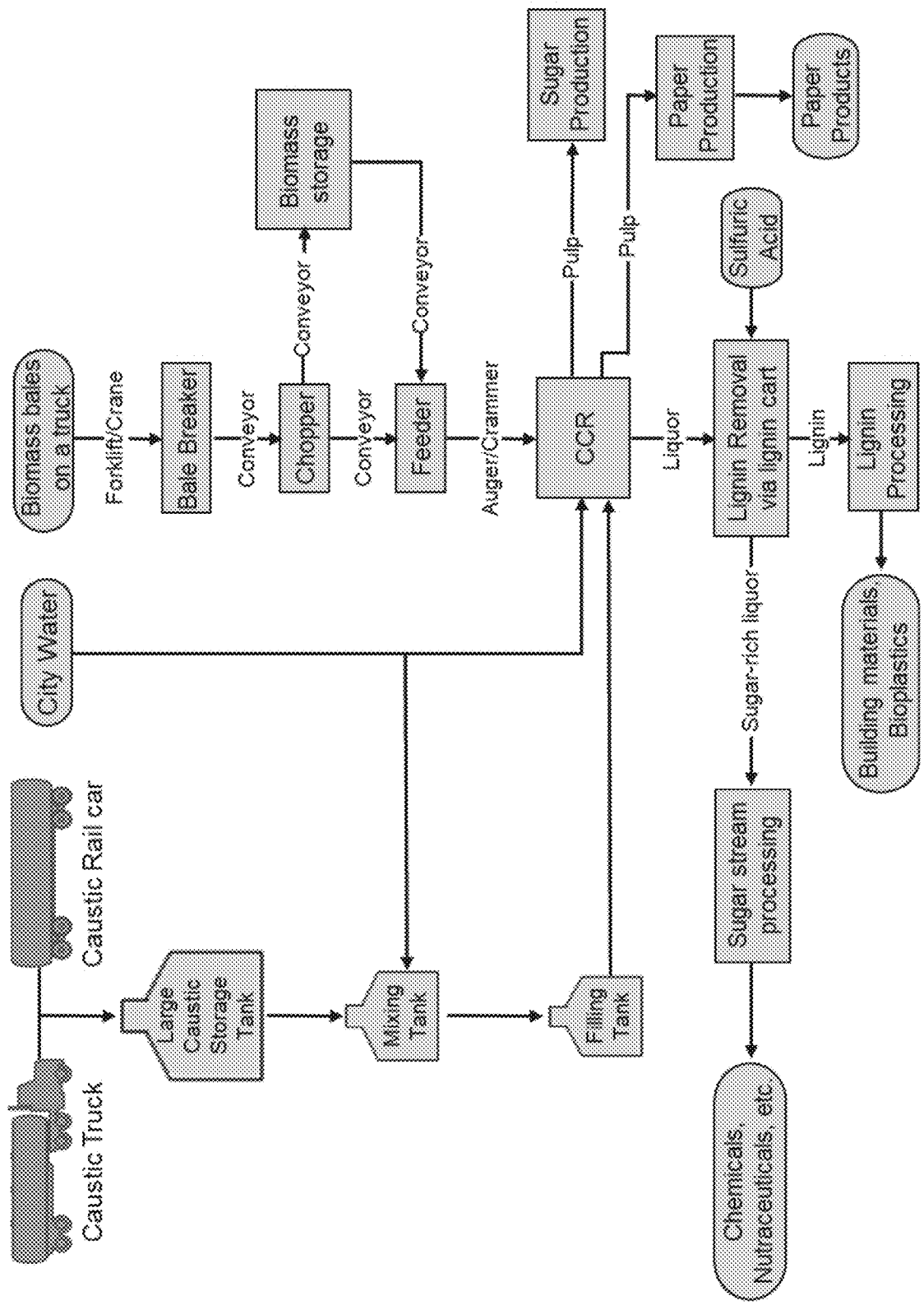
FIG. 2 is a process flow diagram of continuous countercurrent reactor (CCR) biorefining of lignocellulosic biomass to fractionate and produce three distinct product fractions: a first comprising a solid cellulose, a second comprising a solubilized lignin, and a third comprising solubilized hemicellulose (xylose).

The continuous countercurrent reactor allows for processing biomass feedstocks at a wide range from about 0.5 to about 1000 dry tonnes (metric tons; 1000 kg) biomass per day. See FIG. 2. For example, the continuous countercurrent reactor with scale-up can process at least 0.5-ton/day, at least 4-ton/day, at least 8-ton/day, at least 50-ton/day, at least 100-ton/day, at least 200-ton/day, at least 250-ton/day, at least 500-ton/day, at least 1000-ton/day. Size-reduced lignocellulosic feedstock is continuously delivered by a system of augers and forced into one end of the reactor while the needed reagents enter at the opposite end, enabling the liquids and solids to pass one another in counterflow with continuous discharge of a liquid stream near the feedstock inlet and a solid stream at the opposite end of the reactor. The liquid discharge passes through a filtration device which forces most insolubles back into the reactor while allowing the solubilized lignin and xylose-rich liquid to pass through. Countercurrent processing significantly reduces the boundary layer between the feedstock and bulk liquid, allowing hydrolyzed components to quickly enter the bulk liquid and exit the high temperature reaction zone. This reduces product degradation and allows for high-quality xylose recoveries that avoid further xylose degradation to furfural and other inhibition products. The continuous countercurrent reactor screws further shear the biomass and provide mixing while conveying the remaining solids toward the reactor's solid discharge end. A dynamic biomass plug towards each end of the reactor holds pressure during the hydrolysis reaction. The targeted chemistry and heat with corresponding pressures applied within the continuous countercurrent reactor facilitate the removal of lignin and hemicellulose/xylose (C5 sugars) from the feedstock, resulting in a composition of matter comprised largely of cellulose (the cellulose is mostly composed of glucan, which is further monomerized to C6 sugars) and the lignin and xylose-rich liquid discharge product. The solubilized lignin and hemicellulose exit the continuous countercurrent reactor in the liquid discharge and downstream processing isolates these value-added lignin and xylose-rich sugar co-products.

Using a continuous countercurrent reactor affords many processing advantages:
1) multi-stage, stepwise fractionation allows for wide-ranging operating conditions, diverse feedstock and inputs, and modular expansion;
2) integration of several pretreatment, delignification and hydrolysis technologies including thermo-mechanical size-reduction, hot prewash, in situ solid-liquid separation, multiple chemical extractions, and explosive decompression, if desired;
3) continuous countercurrent operation results in independent liquid and solids severities contributing to reduced undesirable byproducts, and improved product concentration and yields compared to conventional co-flow or batch processes;
4) efficient, extremely versatile, easily controllable, and rapid process times; and
5) significantly reduced biorefining footprint allowing for the possibility of modular, skid-mounted units and reduced costs.

In different versions of the method, at least 50%, at least 55%, at least 60%, at least 65%, at least 70%, at least 75%, at least 80%, at least 85%, at least 90%, or at least 96% of the original cellulose in the biomass composition is collected in the continuous countercurrent reactor output solid discharge.

In other versions of the method, the method removes approximately 90% of the lignin present in the raw biomass (e.g., at least 60%, at least 65%, at least 70%, at least 75%, at least 80%, at least 85%, at least 88%, at least 89%, at least 90% of the lignin). In still other versions of the method, the method removes approximately 95% of the hemicellulose present in the raw biomass (e.g., at least 60%, at least 65%, at least 70%, at least 75%, at least 80%, at least 85%, at least 88%, at least 89%, at least 90%, at least 91%, at least 92%, at least 93%, at least 94%, or at least 95%). These product fractions exit the continuous countercurrent reactor liquid discharge.

In another specific version of the method, the cellulose-containing composition of matter produced by the method comprises >85% cellulose by dry weight. It is preferred that the cellulose-containing composition of matter produced by the method comprises at least 50%, at least 55%, at least 60%, at least 65%, at least 70%, at least 75%, at least 80%, at least 85%, or at least 90% by dry weight cellulose.

Figure 3:
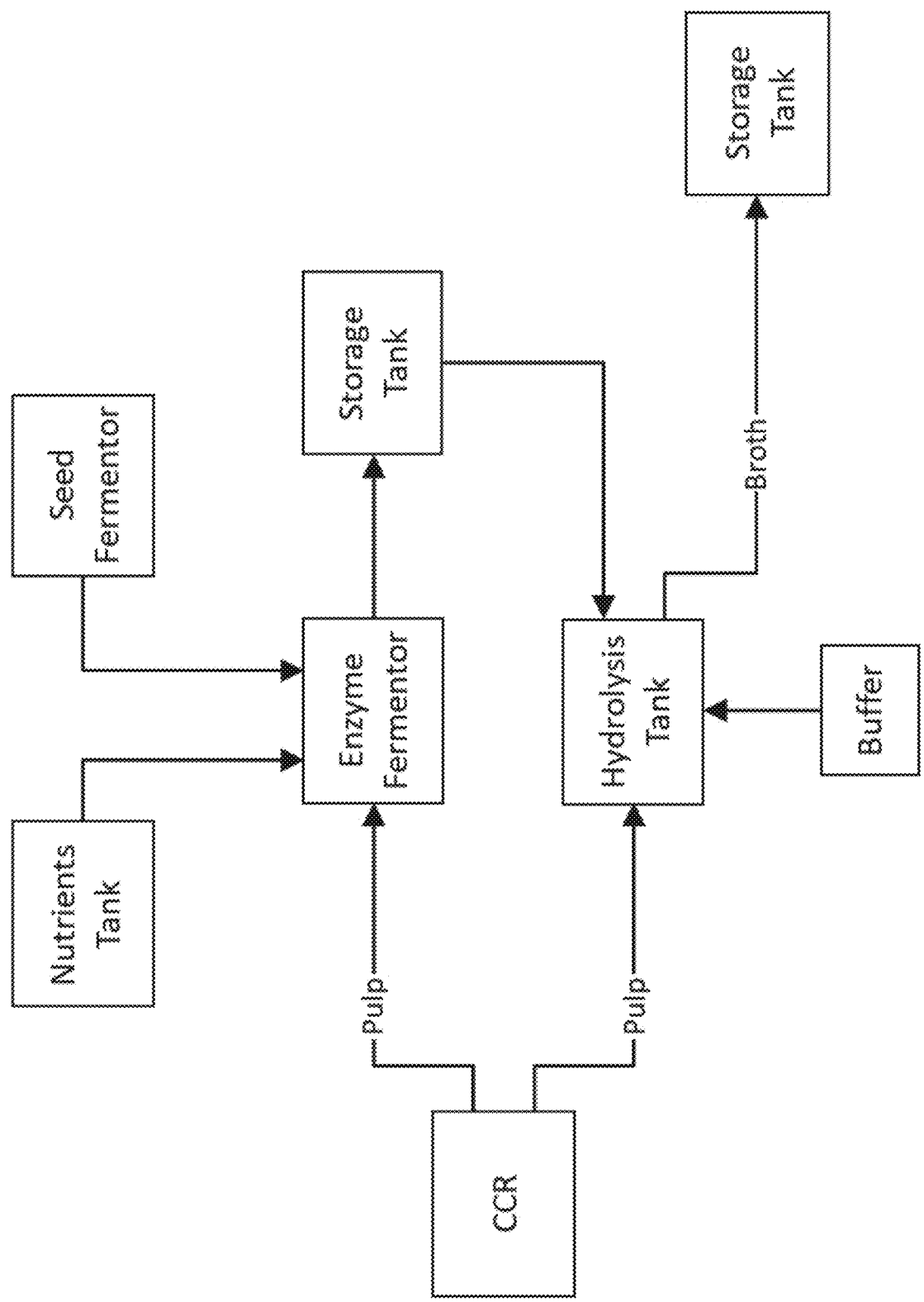
FIG. 3 is a process flow diagram of on-site production of cellulolytic enzymes and in situ enzymatic hydrolysis using the continuous countercurrent reactor-derived cellulose fraction.

Another specific version of the method utilizes a portion of the continuous countercurrent reactor-derived cellulose-containing composition of matter as a substrate for producing cellulolytic enzymes, on site. See FIG. 3. As used herein, the term "cellulolytic enzymes" refers to any enzyme having the EC designation 3.2.1.x:
EC 3.2.1.1: α-amylase
EC 3.2.1.2: β-amylase
EC 3.2.1.3: glucan 1,4-α-glucosidase
EC 3.2.1.4: cellulase
EC 3.2.1.6: endo-1,3 (4)-β-glucanase
EC 3.2.1.7: inulinase
EC 3.2.1.8: endo-1,4-β-xylanase
EC 3.2.1.10: oligo-1,6-glucosidase
EC 3.2.1.11: dextranase
EC 3.2.1.14: chitinase
EC 3.2.1.15: polygalacturonase
EC 3.2.1.17: lysozyme
EC 3.2.1.18: exo-α-sialidase
EC 3.2.1.20: α-glucosidase
EC 3.2.1.21: β-glucosidase
EC 3.2.1.22: α-galactosidase
EC 3.2.1.23: β-galactosidase
EC 3.2.1.24: α-mannosidase
EC 3.2.1.25: β-mannosidase
EC 3.2.1.26: β-fructofuranosidase
EC 3.2.1.28: α,α-trehalase
EC 3.2.1.31: β-glucuronidase
EC 3.2.1.32: xylan endo-1,3-β-xylosidase
EC 3.2.1.33: amylo-1,6-glucosidase
EC 3.2.1.35: hyaluronoglucosaminidase
EC 3.2.1.36: hyaluronoglucuronidase
EC 3.2.1.37: xylan 1,4-β-xylosidase
EC 3.2.1.38: β-D-fucosidase
EC 3.2.1.39: glucan endo-1,3-β-D-glucosidase
EC 3.2.1.40: α-L-rhamnosidase
EC 3.2.1.41: pullulanase
EC 3.2.1.42: GDP-glucosidase
EC 3.2.1.43: β-L-rhamnosidase
EC 3.2.1.44: fucoidanase
EC 3.2.1.45: glucosylceramidase
EC 3.2.1.46: galactosylceramidase
EC 3.2.1.47: galactosylgalactosylglucosylceramidase
EC 3.2.1.48: Sucrose alpha-glucosidase
EC 3.2.1.49: α-N-acetylgalactosaminidase
EC 3.2.1.50: α-N-acetylglucosaminidase
EC 3.2.1.51: α-L-fucosidase
EC 3.2.1.52: β-L-N-acetylhexosaminidase
EC 3.2.1.53: β-N-acetylgalactosaminidase
EC 3.2.1.54: cyclomaltodextrinase
EC 3.2.1.55: α-N-arabinofuranosidase
EC 3.2.1.56: glucuronosyl-disulfoglucosamine glucuronidase
EC 3.2.1.57: isopullulanase
EC 3.2.1.58: glucan 1,3-β-glucosidase
EC 3.2.1.59: glucan endo-1,3-α-glucosidase
EC 3.2.1.60: glucan 1,4-α-maltotetraohydrolase
EC 3.2.1.61: mycodextranase
EC 3.2.1.62: glycosylceramidase
EC 3.2.1.63: 1,2-alpha-L-fucosidase
EC 3.2.1.64: 2,6-β-fructan 6-levanbiohydrolase
EC 3.2.1.65: levanase
EC 3.2.1.66: quercitrinase
EC 3.2.1.67: galacturan 1,4-α-galacturonidase
EC 3.2.1.68: isoamylase EC 3.2.1.70: glucan 1,6-α-glucosidase
EC 3.2.1.71: glucan endo-1,2-β-glucosidase
EC 3.2.1.72: xylan 1,3-β-xylosidase
EC 3.2.1.73: licheninase
EC 3.2.1.74: glucan 1,4-β-glucosidase
EC 3.2.1.75: glucan endo-1,6-β-glucosidase
EC 3.2.1.76: L-iduronidase
EC 3.2.1.77: mannan 1,2-(1,3)-α-mannosidase
EC 3.2.1.78: mannan endo-1,4β-mannosidase
EC 3.2.1.80: fructan β-fructosidase
EC 3.2.1.81: agarase
EC 3.2.1.82: exo-poly-α-galacturonosidase
EC 3.2.1.83: k-carrageenase
EC 3.2.1.84: glucan 1,3-α-glucosidase
EC 3.2.1.85: 6-phospho-β-galactosidase
EC 3.2.1.86: 6-phospho-β-glucosidase
EC 3.2.1.87: capsular-polysaccharide endo-1,3-α-galactosidase
EC 3.2.1.88: β-L-arabinosidase
EC 3.2.1.89: arabinogalactan endo-1,4-β-galactosidase
EC 3.2.1.91: cellulose 1,4-β-cellobiosidase
EC 3.2.1.92: peptidoglycan β-N-acetylmuramidase
EC 3.2.1.93: α,α-phosphotrehalase
EC 3.2.1.94: glucan 1,6-α-isomaltosidase
EC 3.2.1.95: dextran 1,6-α-isomaltotriosidase
EC 3.2.1.96: mannosyl-glycoprotein endo-β-N-acetylglucosaminidase
EC 3.2.1.97: glycopeptide α-N-acetylgalactosaminidase
EC 3.2.1.98: glucan 1,4-α-maltohexaosidase
EC 3.2.1.99: arabinan endo-1,5-α-L-arabinosidase
EC 3.2.1.100: mannan 1,4-mannobiosidase
EC 3.2.1.101: mannan endo-1,6-α-mannosidase
EC 3.2.1.102: blood-group-substance endo-1,4-β-galactosidase
EC 3.2.1.103: keratan-sulfate endo-1,4-β-galactosidase
EC 3.2.1.104: steryl-β-glucosidase
EC 3.2.1.105: strictosidine β-glucosidase
EC 3.2.1.106: mannosyl-oligosaccharide glucosidase
EC 3.2.1.107: protein-glucosylgalactosylhydroxylysine glucosidase
EC 3.2.1.108: lactase
EC 3.2.1.109: endogalactosaminidase
EC 3.2.1.110: mucinaminylserine mucinaminidase
EC 3.2.1.111: 1,3-alpha-L-fucosidase
EC 3.2.1.112: 2-deoxyglucosidase
EC 3.2.1.113: mannosyl-oligosaccharide 1,2-α-mannosidase
EC 3.2.1.114: mannosyl-oligosaccharide 1,3-1,6-α-mannosidase
EC 3.2.1.115: branched-dextran exo-1,2-α-glucosidase
EC 3.2.1.116: glucan 1,4-α-maltotriohydrolase
EC 3.2.1.117: amygdalin β-glucosidase
EC 3.2.1.118: prunasin β-glucosidase
EC 3.2.1.119: vicianin β-glucosidase
EC 3.2.1.120: oligoxyloglucan β-glycosidase
EC 3.2.1.121: polymannuronate hydrolase
EC 3.2.1.122: maltose-6'-phosphate glucosidase
EC 3.2.1.123: endoglycosylceramidase
EC 3.2.1.124: 3-deoxy-2-octulosonidase
EC 3.2.1.125: raucaffricine β-glucosidase
EC 3.2.1.126: coniferin β-glucosidase
EC 3.2.1.127: 1,6-alpha-L-fucosidase
EC 3.2.1.128: glycyrrhizinate beta-glucuronidase
EC 3.2.1.129: endo-α-sialidase
EC 3.2.1.130: glycoprotein endo-α-1,2-mannosidase
EC 3.2.1.131: xylan α-1,2-glucuronosidase
EC 3.2.1.132: chitosanase
EC 3.2.1.133: glucan 1,4-α-maltohydrolase
EC 3.2.1.134: difructose-anhydride synthase
EC 3.2.1.135: neopullulanase
EC 3.2.1.136: glucuronoarabinoxylan endo-1,4-β-xylanase
EC 3.2.1.137: mannan exo-1,2-1,6-α-mannosidase
EC 3.2.1.139: Alpha-glucuronidase
EC 3.2.1.140: lacto-N-biosidase
EC 3.2.1.141: 4-α-D-((1-4)-α-D-glucano)trehalose trehalohydrolase
EC 3.2.1.142: limit dextrinase
EC 3.2.1.143: poly(ADP-ribose) glycohydrolase
EC 3.2.1.144: 3-deoxyoctulosonase
EC 3.2.1.145: galactan 1,3-β-galactosidase
EC 3.2.1.146: β-galactofuranosidase
EC 3.2.1.147: thioglucosidase
EC 3.2.1.149: β-primeverosidase
EC 3.2.1.150: oligoxyloglucan reducing-end-specific cellobiohydrolase
EC 3.2.1.151: xyloglucan-specific endo-β-1,4-glucanase
EC 3.2.1.152: mannosylglycoprotein endo-β-mannosidase
EC 3.2.1.153: fructan β-(2,1)-fructosidase
EC 3.2.1.154: fructan β-(2,6)-fructosidase
EC 3.2.1.155: xyloglucan-specific exo-beta-1,4-glucanase
EC 3.2.1.156: oligosaccharide reducing-end xylanase
EC 3.2.1.157: iota-carrageenase
EC 3.2.1.158: alpha-agarase
EC 3.2.1.159: alpha-neoagaro-oligosaccharide hydrolase
EC 3.2.1.161: beta-apiosyl-beta-glucosidase
EC 3.2.1.162: lambda-carrageenase
EC 3.2.1.163: 1,6-alpha-D-mannosidase
EC 3.2.1.164: galactan endo-1,6-beta-galactosidase
EC 3.2.1.165: exo-1,4-beta-D-glucosaminidase
EC 3.2.1.166: blood group B branched chain alpha-1,3-galactosidase
EC 3.2.1.167: blood group B linear chain alpha-1,3-galactosidase
EC 3.2.1.168: hesperidin 6-O-alpha-L-rhamnosyl-beta-D-glucosidase
EC 3.2.1.169: protein O-GlcNAcase
EC 3.2.1.170: mannosylglycerate hydrolase
EC 3.2.1.171: rhamnogalacturonan hydrolase
EC 3.2.1.172: unsaturated rhamnogalacturonyl hydrolase
EC 3.2.1.173: rhamnogalacturonan galacturonohydrolase
EC 3.2.1.174: rhamnogalacturonan rhamnohydrolase
EC 3.2.1.175: beta-D-glucopyranosyl abscisate beta-glucosidase
EC 3.2.1.176: cellulose 1,4-beta-cellobiosidase (reducing end)
EC 3.2.1.177: alpha-D-xyloside xylohydrolase
EC 3.2.1.178: beta-porphyranase
EC 3.2.1.179: gellan tetrasaccharide unsaturated glucuronyl hydrolase
EC 3.2.1.180: unsaturated chondroitin disaccharide hydrolase
EC 3.2.1.181: galactan endo-beta-1,3-galactanase
EC 3.2.1.182: 4-hydroxy-7-methoxy-3-oxo-3,4-dihydro-2H-1,4-benzoxazin-2-yl glucoside beta-D-glucosidase
EC 3.2.1.183: UDP-N-acetylglucosamine 2-epimerase (hydrolysing)
EC 3.2.1.184: UDP-N,N'-diacetylbacillosamine 2-epimerase (hydrolysing)

Exemplary enzymes include, but are not limited to cellobiohydrolase (CBH), endoglucanase (EG), and β-glucosidase (BG); by aerobic fermentation using microorganisms, such as *Trichoderma reesei*. Note that *T. reesei* is exemplary and the while aerobic fermentation is preferred (it is easier), the method encompasses anaerobic fermentation as well.

Figure 4:
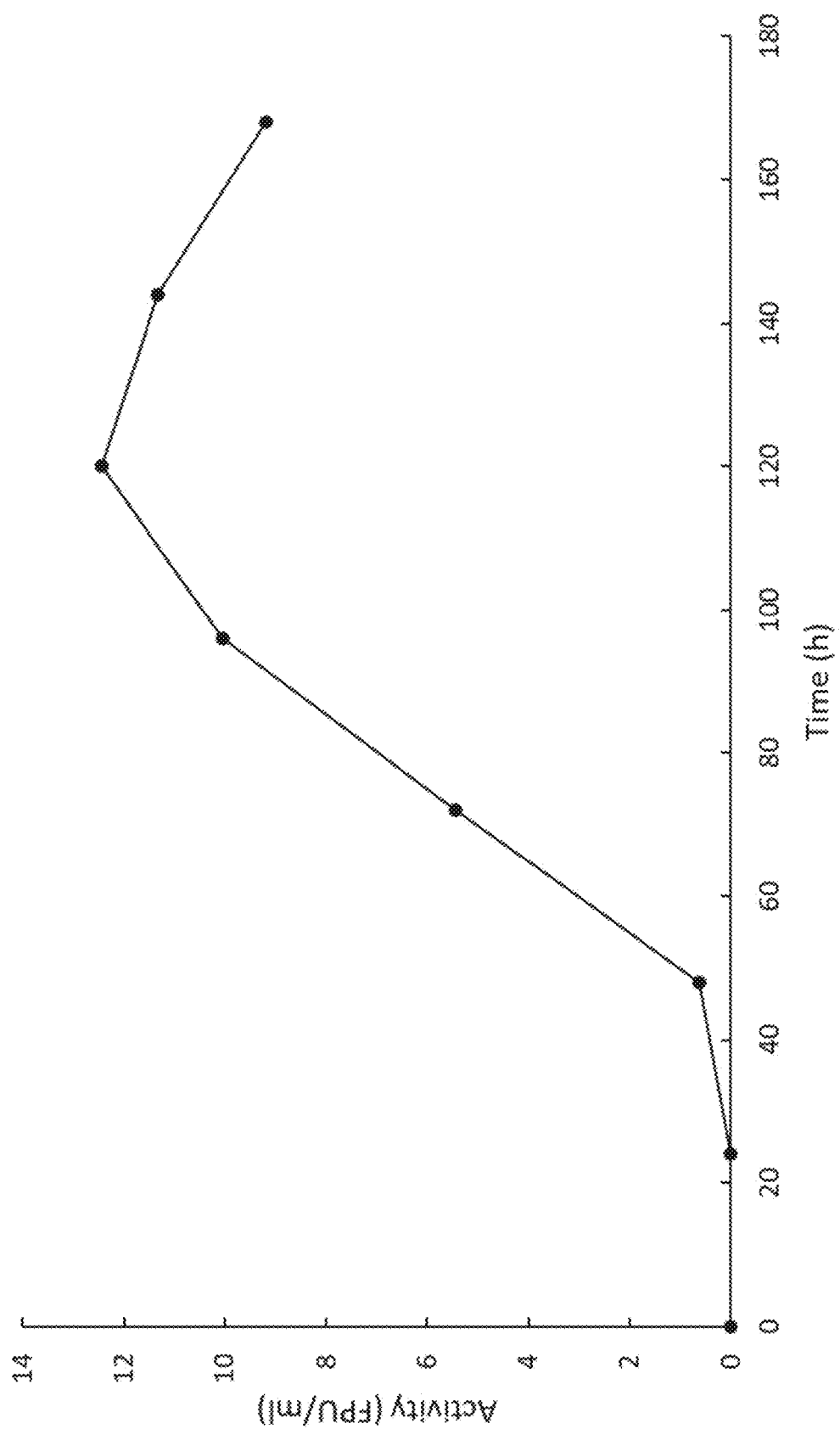
FIG. 4 is a graph depicting enzyme activity in filter paper units per milliliter ("FPU/ml") of cellulase and/or cellulolytic enzyme cocktail produced from continuous countercurrent reactor-derived hemp cellulose as the substrate.

The microorganism chosen for fermentation is unlimited and includes both prokaryotes (for example *Lactobacillus* bacteria, including, but not limited to *Lactococcus lactis, L. cremoris, L. diacetilactis, L. thermophilus, Lactobacillus lactis, L. bulgaricus, L. acidophilus*, etc.) and eukaryotes (for example suitable yeasts, such as those of the genus *Saccharomyces*, for example, *S. cerevisiae, S. paradoxus, S. bayanus, S. cerevisiae* var *boulardii*, etc.). The microorganism might also be selected from coryneform *Propionibacterium, Veillonella, Clostridium,* Selenomonas, etc., such as *Propionibacterium acidipropionici, P. freudenreichii,* etc. The method further provides for treating the remaining continuous countercurrent reactor-derived cellulosic material with cellobiohydrolase 1 and 2, endoglucanase, and/or β-glucosidase, or to such purified cellulolytic enzyme cocktails, or to such crude cellulolytic enzyme cocktails, or to an equivalent enzymatically active fragment thereof. See FIG. 4. Using these on-site enzyme preparations for hydrolyzing continuous countercurrent reactor-derived cellulosic material is also within the scope of the method, as well as using the method in processes for preparing ethanol, lactic acid, and other fermentation products from cellulosic derived fermentation sugars.

Figure 5:
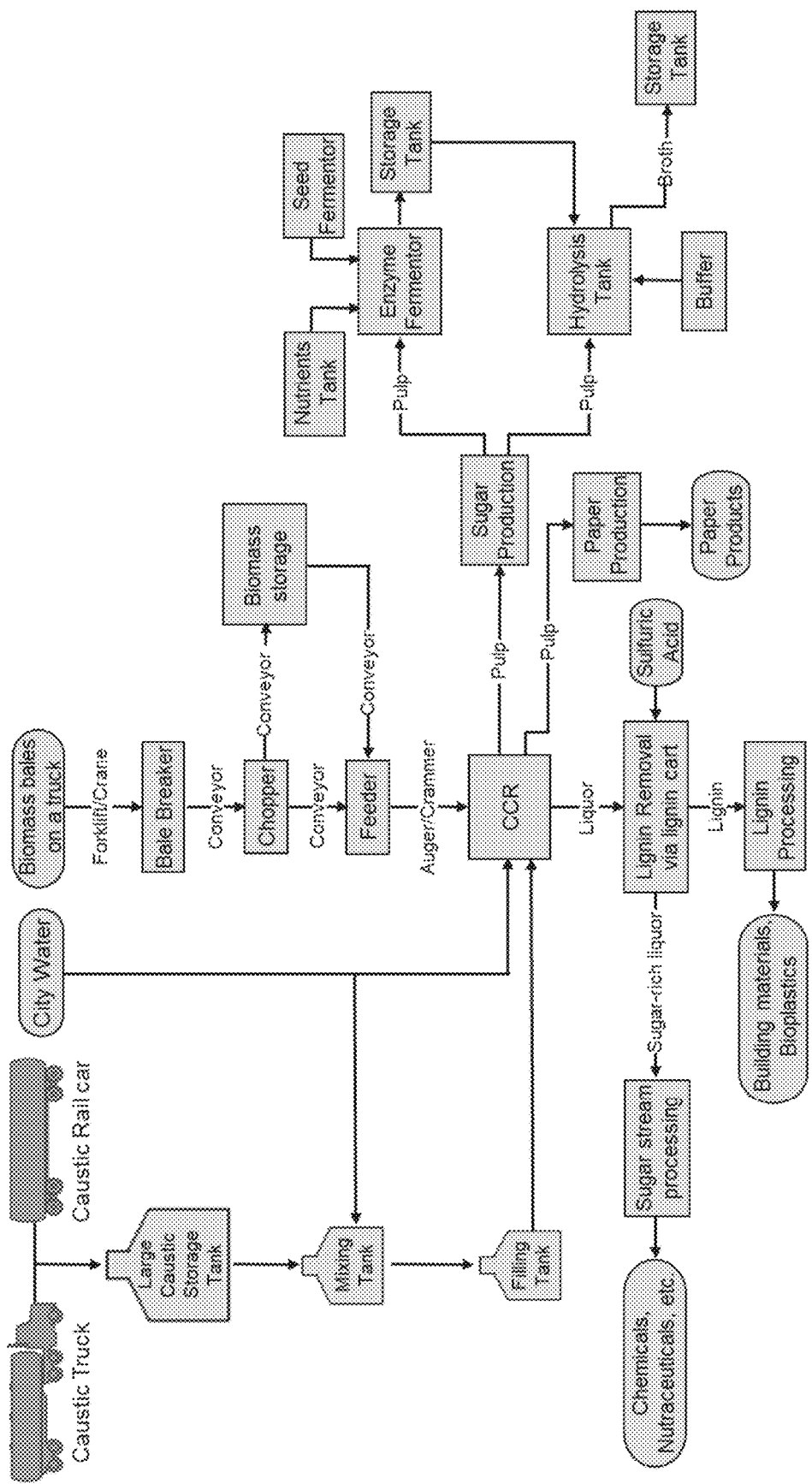
FIG. 5 is a process flow diagram of an integrated system to treat cellulosic biomass to produce cellulose, to on-site cellulase production, and to in-situ enzymatic hydrolysis.

Also disclosed is an integrated process wherein a continuous countercurrent reactor is operated under improved hydrothermal pretreatment conditions to produce cellulose-containing compositions of matter of reduced lignin content (reduced as compared to the native biomass) from various biomass feedstocks such as wheat straw, corn stalks, poplar wood chips, hemp stalks, and the like; followed by a process using a portion of the resulting cellulose compositions of matter to undergo fermentation using microorganisms such as *T. reesei* for on-site cellulolytic enzyme production. The process to this point can optionally be vertically integrated into a process that uses the resulting crude fungal fermentation broth for enzymatic hydrolysis to convert the remaining cellulose into inexpensive sugars. See FIG. 5. Certain aspects of the integrated process describe using continuous countercurrent reactor-derived hemicellulose rich liquor obtained from post-lignin recovery of the continuous countercurrent reactor liquid discharge fraction, as the liquid medium, either used in un-detoxified or detoxified form to be added to the fermentation broth, for in situ enzymatic hydrolysis of the cellulose fraction. This additional step yields mixed C5- and C6-sugars. These sugars can be used for any purpose, such as further fermentation to ethanol and/or lactic acid, or other chemicals.

Figure 7:
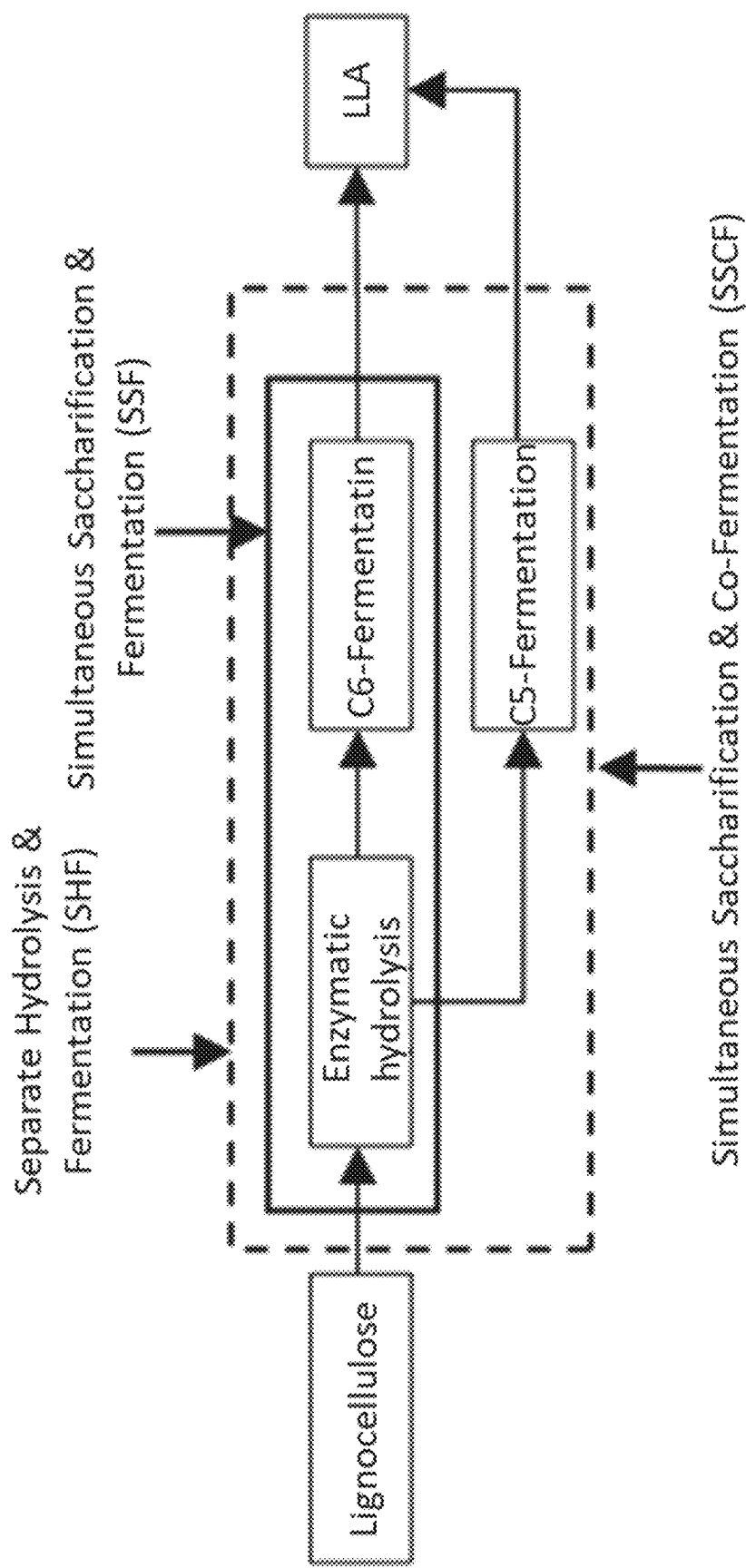
FIG. 7 is a schematic diagram illustrating process boundary of Separate Hydrolysis & Fermentation (SHF), Simultaneous Saccharification & Fermentation (SSF) and Simultaneous Saccharification & Co-Fermentation (SSCF) of both continuous countercurrent reactor-derived C5- and C6-sugar streams to produce lactic acid.
Figure 8:
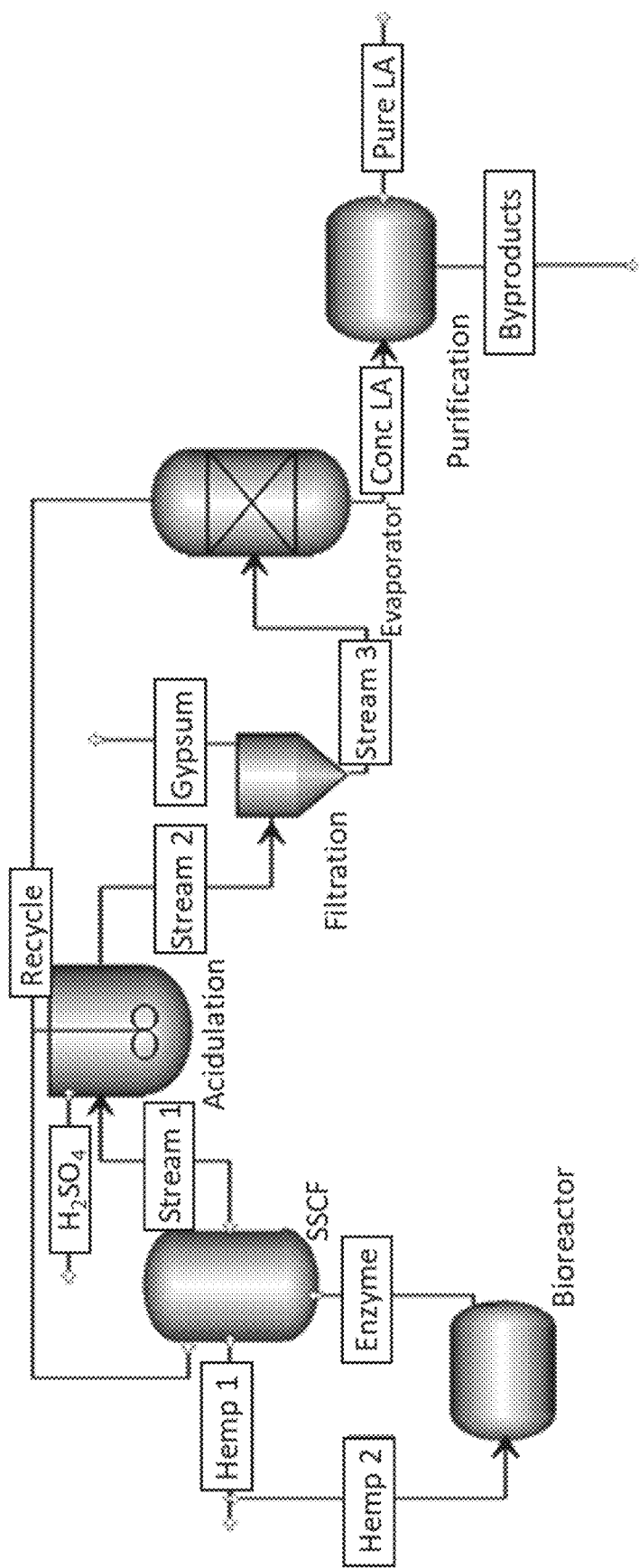
FIG. 8 is a process flow diagram showing integrating the production of cellulase enzymes and lactic acid simultaneously from continuous countercurrent reactor-derived cellulose.

The method may also integrate co-fermentation processes using *Saccharomyces cerevisiae, Bacillus coagulans, Lactobacillus pentosus,* etc. to the coupled cellulase fermentation-enzymatic hydrolysis process to respectively produce ethanol and/or lactic acid, directly from the continuous countercurrent reactor-derived cellulose fractions. In particular embodiments, the processes that integrate co-fermentation with enzymatic hydrolysis (see FIGS. 7 and 8) to produce ethanol and lactic acid include:

1) Separate Hydrolysis & Fermentation (SHF);
2) Simultaneous Saccharification & Fermentation (SSF); and
3) Simultaneous Saccharification & Co-Fermentation (SSCF).

Specifically preferred versions of the method utilize >25% of the continuous countercurrent reactor-derived cellulose to produce crude cellulolytic enzyme cocktails. Other versions may utilize less of the cellulose fraction for this purpose, for example at least 5%, at least 10%, at least 15%, or at least 20%. Related aspects provide methods for using at least 35%, at least 40%, at least 45%, at least 50%, at least 55%, at least 60%, at least 65%, or at least 75% of continuous countercurrent reactor-derived cellulose to produce sugars via in situ enzymatic hydrolysis.

One illustrative version of the method yields crude cellulase enzyme preparations using continuous countercurrent reactor-derived cellulose as a substrate. The enzyme preparation exhibited cellulase activity from about 9.2 FPU/mL to about 12.4 FPU/mL. See FIG. 4. The yield of the corresponding cellulase enzymes in the crude fermentation broth was 262.9 FPU/g-glucan to 354.3 FPU/g-glucan.

Figure 10:
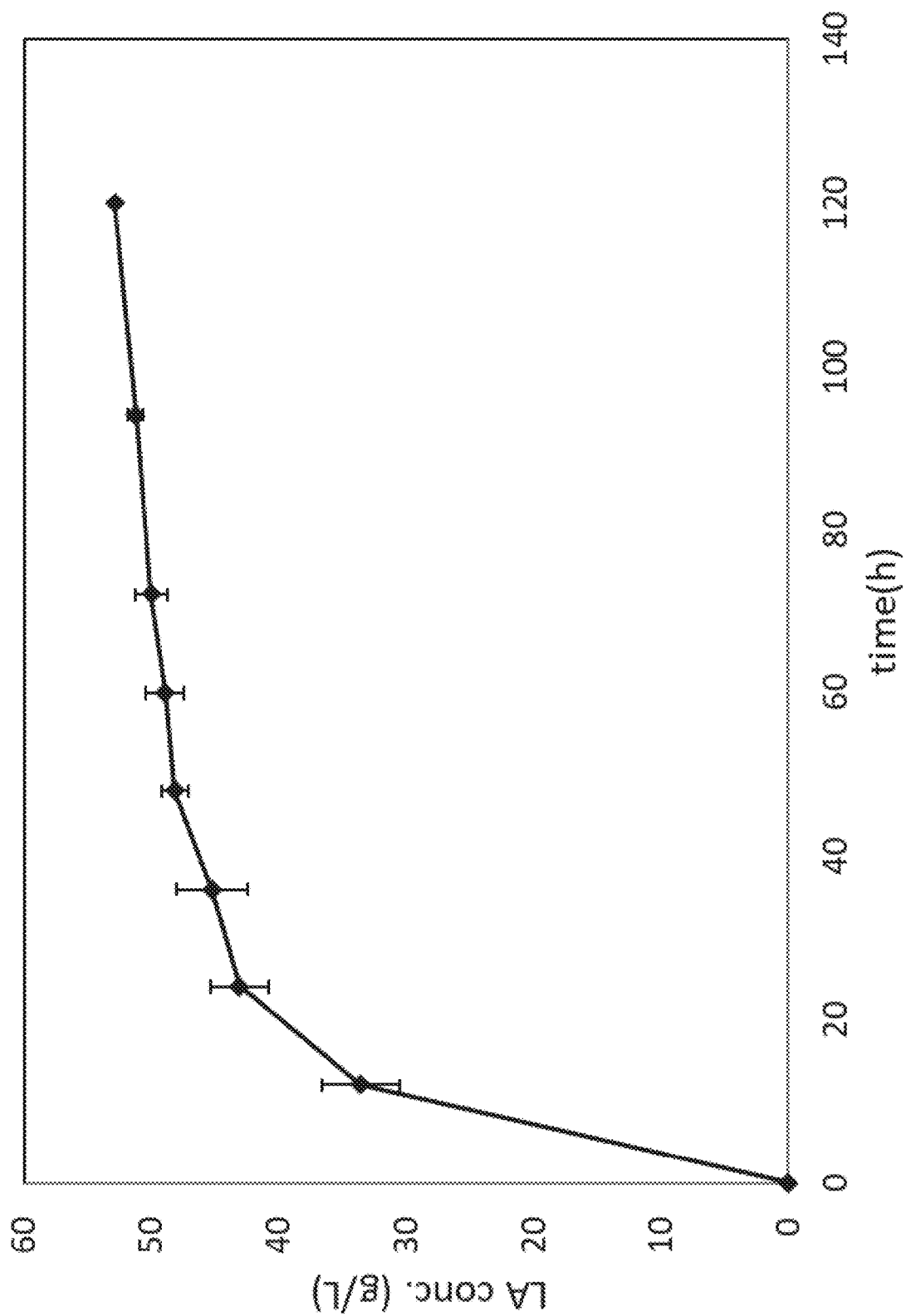
FIG. 10 is a graph showing lactic acid production from continuous countercurrent reactor-derived pulp in Simultaneous Saccharification & Co-Fermentation (SSCF) process.

For in situ enzymatic hydrolysis of the cellulose fraction using crude fermentation broth, the substrate loading may range from about 5% to about 10%, with enzyme loadings at about 15 FPU/g-glucan. Under these conditions, overall glucan digestibility ranged from about 59.8% to about 70.0%. Correspondingly, the average glucose production from continuous countercurrent reactor-derived cellulose ranged from 58.5 g/L to 68.6 g/L. Xylose yields using the hemicellulose-rich liquor from the reactor were 2.9 g/L to 3.1 g/L. Lactic acid yield reached a maximum of 56.9% of theoretical. A concentration of 53.0 g/L lactic acid was achieved with continuous countercurrent reactor-derived pulp (10% (w/v) solid loading), along with 8.5% (w/v) glucan and 0.03% (w/v) of xylan feed during the co-fermentation process. See FIG. 10.

EXAMPLES

Example 1

Recovery of Purified Cellulose from Agricultural Residues

This example describes using a continuous countercurrent reactor to convert agricultural residues such as hemp stalks to a substantially delignified cellulose product. Hemp feedstocks were Colorado-grown and made available from local farmers. The hemp stalks were size reduced through a ½-inch screen prior to processing them in the continuous countercurrent reactor. A sample of the feedstock was analyzed for its composition by National Renewable Energy Laboratory (NREL) procedures for determining biomass composition. The results of Colorado-grown hemp feedstock can be found in Table 1.

TABLE 1

| Hemp stalk feedstock composition on a dry weight basis. | | |
|---|---|---|
| Component | Assay: (ASTM E1758-01 and E1755-01) | Std. Dev. |
| Glucan | 47.27 | 1.42 |
| Xylan | 12.55 | 0.52 |
| Mannan | 3.19 | 0.13 |
| Ash | 3.21 | 0.04 |
| Klason Lignin | 13.45 | 0.81 |
| Non-Sugar Extractives | 7.42 | 0.26 |
| Sum | 87.09 | 0.42 |

The continuous countercurrent reactor was operated at 208° C. and with a sodium hydroxide (NaOH) loading of 15% (wt/wt %) of the dry hemp feedstock rate. The full list of continuous countercurrent reactor operating conditions can be found in Table 2. The continuous countercurrent reactor was able to operate stably at this condition and enabled collection of cellulosic fibers and/or pulp samples (run ID 066-03-11). The corresponding hemp pulp sample was analyzed for composition (Table 3) per NREL Standard Biomass Analytical Procedures [TAPPI test method (T22-om 88)]. The hemp pulp was found to be of high purity cellulose with low lignin content and was therefore considered as a potential substrate for both on-site cellulase production and in situ enzymatic hydrolysis to produce hemp derived fermentable sugars.

TABLE 2

Pilot-scale continuous countercurrent reactor operating conditions for run 066-03-11.

| Condition | Measured Value |
| --- | --- |
| Feed Rate (dry g/min) | 121.3 |
| Liquid/Solids (L/S) Ratio (wt/wt) | 5.1 |
| NaOH Loading (wt % of feedstock) | 14.7 |
| NaOH Loading (wt % of total liquid) | 2.9 |
| Average Internal continuous countercurrent reactor Temperature (° C.) | 207.9 |

TABLE 3

Hemp pulp composition on a dry weight basis.

| Component | 066-03-11 Bulk (wt %) | Std. Dev. |
| --- | --- | --- |
| Glucan | 84.6 | 0.07 |
| Xylan | 3.29 | 0.09 |
| Mannan | ND | NA |
| Ash | 4.37 | 0.06 |
| Klason Lignin | 4.34 | 0.05 |

Example 2

Preparation of Xylose (C5) Rich Sugar Syrup from Post Lignin Recovered Mother Liquor This example describes preparing a xylose-rich syrup from the continuous countercurrent reactor liquid discharge stream. The continuous countercurrent reactor-derived, post-lignin recovered mother liquor (ML) was used as the starting material to create a C5-enriched monomeric sugar syrup solution. The composition of post lignin-precipitated ML feedstock is presented in Table 4.

TABLE 4

Estimated percent weight of component per weight of post lignin-precipitated ML

| NVS | Glucose | Xylose | Galactose | Arabinose | Mannose | Total Sugars |
| --- | --- | --- | --- | --- | --- | --- |
| 1.29% | 0.05% | 0.19% | 0.02% | 0.06% | 0.01% | 0.33% |

Consequently, the ML from the lignin precipitation was first acidified to 3% (w/w) $H_2SO_4$ and heated at 120° C. for 1 hour to hydrolyze the oligomeric sugars. The pH of the hydrolysate was adjusted to pH 5.2 with $CaCO_3$ and then chilled overnight at 5° C. prior to vacuum filtration (VWR #417, 40μ) to remove the insoluble calcium salts. The filtrate was rotary evaporated in vacuo at 55° C., then chilled at 5° C. overnight and vacuum filtered again (VWR #413, 5 μm) to remove the precipitated solids. The clarified syrup was sterile filtered (Nalgene #595-3320, 0.2 μm) with a water wash to produce concentrated syrup (Table 5) for fermentation testing.

TABLE 5

Non-volatile solids (NVS), Ash, and Sugars concentration (g/Kg syrup) of final sugar syrup

| NVS | Ash | Glucose | Xylose | Galactose | Arabinose | Mannose | Total Sugars |
| --- | --- | --- | --- | --- | --- | --- | --- |
| 323.36 | 192.88 | 7.46 | 51.71 | NA | 15.74 | 1.86 | 76.78 |

Example 3

Cellulolytic Enzyme Activity Produced from Continuous Countercurrent Reactor-Derived Hemp Cellulose This example describes the cellulolytic enzyme production from continuous countercurrent reactor derived cellulose. This enzyme cocktail (with or without purification) can be used for in situ sugar production or chemical production.

Materials and Methods: 3.5% glucan contained in continuous countercurrent reactor derived pulp was loaded into a 3-liter bioreactor. The temperature was 28° C. and the dissolved oxygen was set at 25% of the saturation throughout the fermentation, pH was controlled with ammonia at 3.5. The enzymatic activity was measured according to the National Renewable Energy Lab procedure (Adney & Baker, 1996).

Results: The enzyme secretion showed a lag-phase of approximately 24 hours and started to display an enzyme production from the second day. It reached the maximum activity (12.4 FPU/ml) at 120 hours and declined thereafter. The decrease of enzyme activity suggested stopping the fermentation at an earlier stage (e.g. at about 120 hr) to avoid the loss of enzyme activity. See FIG. 4.

Example 4

Glucan Digestibility on Enzymatic Hydrolysis of Continuous Countercurrent Reactor-Derived Cellulose with On-Site Cellulases This example describes the sugar production from hemp cellulose using on-site cellulolytic enzymes. Novozyme 188 was added into the cocktail to overcome the accumulation of cellobiose due to the insufficiency of β-glucosidase.

Materials and Methods: The enzymatic hydrolysis was carried out in a 125 mL flask with a working volume of 50 mL. The substrate loading was 10% (w/v) and enzyme loading was 10 FPU/g glucan. The commercial cellulolytic enzymes Celic C-Tec 2 (Novozymes) was applied for comparison purpose. The hydrolysis was conducted at pH 4.8 and buffered with 50 mM sodium citrate, at a temperature of 50° C., with stirring at 180 rpm.

Figure 6:
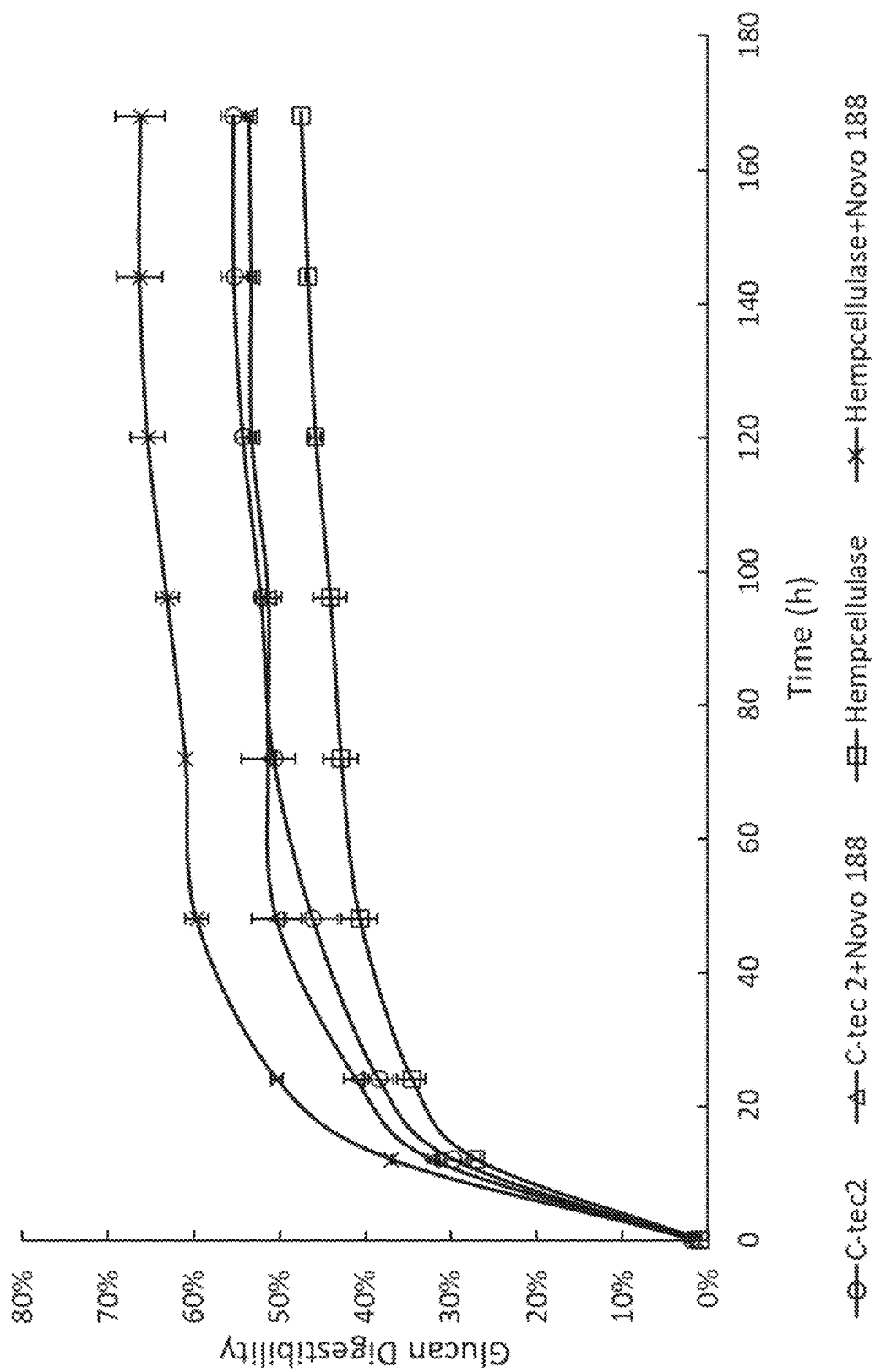
FIG. 6 is a graph comparing glucan digestibility on enzymatic hydrolysis of continuous countercurrent reactor-derived cellulose with on-site cellulases and other commercially available cellulolytic enzyme and enzyme cocktails.

Results: The on-site cellulase had competitive overall glucan digestibility (55.4% vs 47.5%) with the commercial product. The glucan digestibility increased to 66.2% with supplementation of β-glucosidase indicating the inhibition of cellobiose was strong. Additionally, the hydrolysis reached the maximum at approximately 72 hours. See FIG. 6.

Example 5

Effect of Both Detoxified and Un-Detoxified Post Lignin Recovered Hemicellulose Rich Liquor on Enzymatic Hydrolysis and Lactic Acid Fermentation This example describes lactic acid fermentation of enzymatic hydrolysate obtained from continuous countercurrent reactor-derived cellulose. The hemicellulose-rich liquor (post-lignin removal) was integrated into this novel process as a fermentation broth supplement, in a detoxified and un-detoxified form, to increase the C5 sugar utilization and reduce freshwater usage.

Materials and Methods: The whole slurry obtained from enzymatic hydrolysis was supplemented with 1 g/L $(NH_4)_2SO_4$, 0.4 g/L $KH_2PO_4$, 0.3 g/L $MgSO_47H_2O$, 2.5 g/L NaCl and 20 g/L yeast extract. The fermentation was carried out at 50° C. with a working volume of 60 mL. 3 g $CaCO_3$ was added to control the pH. The inoculum was 10% (v/v). The overliming detoxification was conducted by adding $Ca(OH)_2$ to pH 10 and kept at 60° C. for 2 hours.

Figure 9:
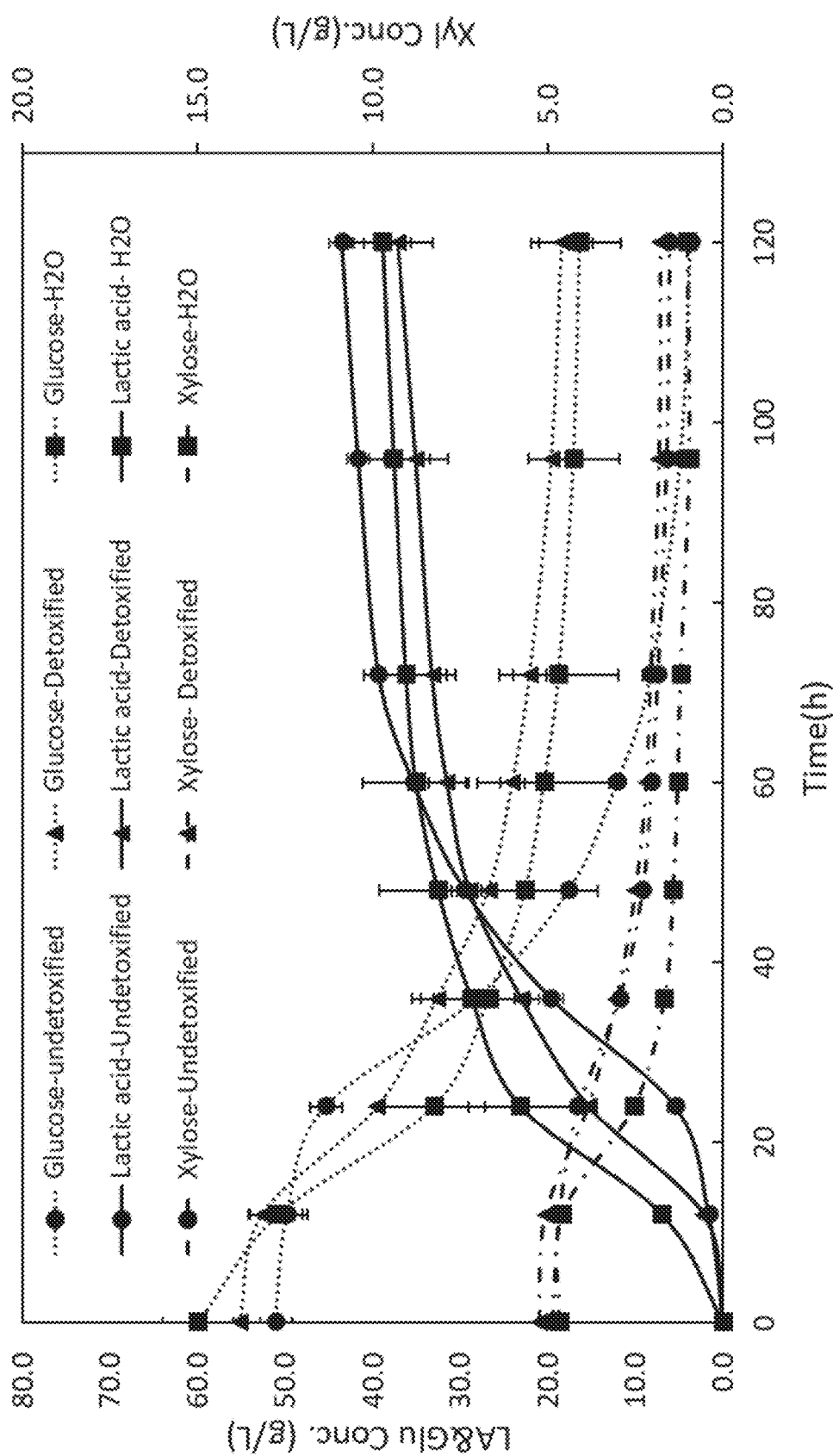
FIG. 9 is a graph depicting the effect of detoxified and un-detoxified post-lignin recovery, hemicellulose-rich liquor on Separate Hydrolysis & Fermentation (SHF) processing of continuous countercurrent reactor-derived cellulose to xylose (C5), glucose (C6) and lactic acid respectively.

Results: The hydrolysate supplemented with undetoxified liquor showed the lowest initial fermentation rate but the highest final yield (43.6%) and the sugars in the broth were almost gone. This suggests the microbes may have established resistance to the toxicity of the undetoxified liquor (or accessed an alternative metabolic pathway) as the fermentation progressed. This is a salutary outcome as it shows that detoxification of the liquor, while still beneficial, is not necessary to achieve a high final yield. In the meantime, the C5 sugar in the liquor was used as a carbon source to increase lactic acid production. See FIG. 9.

Example 6

Lactic Acid Production from Continuous Countercurrent Reactor-Derived Pulp in SSCF Process This example describes producing lactic acid from continuous countercurrent reactor derived pulp in the SSCF process. This process surmounts the enzymatic hydrolysis step and converts both cellulose and hemicellulose directly to lactic acid.

Materials and Methods: The cellulose-containing fraction derived from continuous countercurrent reactor pretreatment was used as the substrate. It was loaded at 10% (w/v) and 20 g/L yeast extract was added to provide nutrients. The enzyme loading was 10 FPU/g glucan and inoculum was 5% (v/v). The fermentation was carried out at 37° C. with a working volume of 60 mL. 3 g $CaCO_3$ was added to control the pH.

Results: The final LA concentration at 120 h was 53.0 g/L, corresponding to a yield of 56.9%. See FIG. 10.

The foregoing discussion has been presented for purposes of illustration and description. The foregoing is not intended to limit the disclosed method to the form or forms disclosed herein. Although the description of the method has included description of several versions, variations, and modifications, other variations and modifications are within the scope of the claims, e.g., as may be within the skill and knowledge of those in the art, after understanding the present disclosure. It is intended to obtain rights which include alternative versions to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more."

All combinations of method or process steps as used herein can be performed in any order, unless otherwise specified or clearly implied to the contrary by the context in which the referenced combination is made.

The methods disclosed herein may comprise, consist of, or consist essentially of the necessary elements and limitations disclosed herein, as well as any additional or optional, steps, ingredients, components, or limitations described herein or otherwise useful in processing raw biomass into monomeric sugars.

REFERENCES

Adney, B., Baker, J. (1996) "Measurement of cellulase activities," *Laboratory analytical procedure*, 6(465): 1996.
Lee et al., U.S. Pat. No. 8,900,457, "Fermentation and chemical treatment of pulp and paper mill sludge," issued Dec. 2, 2014.
Wingerson, U.S. Pat. No. 6,419,788, "Method of treating lignocellulosic biomass to produce cellulose," issued Jul. 16, 2002.
Wingerson, U.S. Pat. No. 6,620,292, "Cellulose production from lignocellulosic biomass," issued Sep. 16, 2003
Wingerson, U.S. Pat. No. 7,600,707, "Apparatus for the separation and treatment of solid biomass," issued Oct. 13, 2009.
Wingerson, U.S. Pat. No. 7,717,364, "Apparatus for the separation and treatment of solid biomass," issued May 18, 2010.
Wingerson, U.S. Pat. No. 8,136,747, "Apparatus for separation and treatment of solid biomass," issued Mar. 20, 2012.

What is claimed is:

1. A method of making and using enzymes in situ, the method comprising:
   (a) in a continuous, counter-current extruder/reactor, admixing biomass and water for a time, and a temperature, and at an energy input, wherein a first, solid-phase composition of matter enriched in cellulose fibers is extruded from a first outlet of the extruder/reactor, and a second, liquid-phase composition of matter enriched in lignin and hemicellulose-derived xylose is extruded from a second outlet of the extruder reactor;
   (b) fermenting in a vessel at least a portion of the first, solid-phase composition of matter with a microorganism capable of fabricating a desired cellulolytic enzyme using cellulose or hemicellulose as a source of carbon, for a time and at a temperature to yield a third composition of matter comprising the desired cellulolytic enzyme;
   (c) in the vessel of step (b), using the third composition of matter to enzymatically hydrolyze remaining cellulose or hemicellulose to yield a fourth composition of matter comprising monomeric sugars.

2. The method of claim 1, further comprising:
   (d) fermenting at least a portion of the monomeric sugars present in the fourth composition of matter.

3. The method of claim 2, wherein in step (d) is conducted in the vessel used in steps (b) and (c).

4. The method of claim 1, wherein in step (a) the water further comprises an acid dissolved therein.

5. The method of claim 1, wherein in step (a) the water further comprises a base dissolved therein.

6. The method of claim 1, wherein in step (a) the biomass and the water are admixed at a temperature of from about 150° C. to about 300° C.

\* \* \* \* \*